United States Patent
Monaco (10) Patent No.: US 12,122,757 B2
(45) Date of Patent: Oct. 22, 2024

(54) CANNABIDIOL EXTRACTION AND CONVERSION PROCESS

(71) Applicant: CLS LABS, INC., Miami, FL (US)

(72) Inventor: Dominick Monaco, Las Vegas, NV (US)

(73) Assignee: CLS LABS, INC., Miami, FL (US)

( * ) Notice: Subject to any disclaimer, the term of this patent is extended or adjusted under 35 U.S.C. 154(b) by 538 days.

(21) Appl. No.: 17/535,389

(22) Filed: Nov. 24, 2021

(65) Prior Publication Data

US 2023/0159483 A1    May 25, 2023

(51) Int. Cl.
   *C07D 311/80*    (2006.01)
(52) U.S. Cl.
   CPC .................................. *C07D 311/80* (2013.01)
(58) Field of Classification Search
   CPC .................................................... C07D 311/80
   See application file for complete search history.

(56) References Cited

U.S. PATENT DOCUMENTS

| | | | |
|---|---|---|---|
| 6,403,126 B1 | 6/2002 | Webster et al. | |
| 7,399,872 B2 | 7/2008 | Webster et al. | |
| 7,510,157 B2 | 3/2009 | Oliver | |
| 7,674,922 B2 * | 3/2010 | Burdick | C07C 29/00 549/390 |
| 9,950,976 B1 | 4/2018 | Keller | |
| 10,582,789 B2 | 3/2020 | Klugh et al. | |
| 11,110,372 B2 * | 9/2021 | Farokhi | B01D 11/0292 |
| 11,220,653 B2 * | 1/2022 | Yao | C11B 1/106 |
| 11,472,758 B2 * | 10/2022 | Shields | B01D 53/228 |
| 2002/0086438 A1 | 7/2002 | Elsohly et al. | |
| 2003/0017216 A1 | 1/2003 | Schmidt et al. | |
| 2004/0049059 A1 | 3/2004 | Mueller | |
| 2005/0266108 A1 | 12/2005 | Flockhart et al. | |
| 2006/0167283 A1 | 7/2006 | Flockhart et al. | |
| 2014/0110202 A1 | 4/2014 | Vesterby | |
| 2021/0100385 A1 | 4/2021 | Delaney | |

* cited by examiner

*Primary Examiner* — Golam M Shameem
(74) *Attorney, Agent, or Firm* — MALLOY & MALLOY, P.L.

(57) ABSTRACT

A cannabidiol extraction and conversion process includes an extraction process including a sizing unit wherein raw *Cannabis* plant material is reduced to a uniform size, a blending unit wherein a first extraction solvent is blended together with the *Cannabis* plant material to form an initial extract including crude CBD oil, and a liquid-liquid extractor unit wherein a second solvent is added to the initial extract, and a processed extract rich in cannabidiol is obtained. A conversion process includes a conversion rotary reflux unit wherein the at least partially processed and refined extract is titrated with an acidic component.

18 Claims, 5 Drawing Sheets

CANNABIDIOL EXTRACTION AND CONVERSION PROCESS

BACKGROUND OF THE INVENTION

Field of the Invention

The present invention is directed to a process for the extraction of cannabidiol from any of a variety of plants of the genus *Cannabis*, including but not limited to industrial hemp varieties which have been specifically bred to substantially limit the amount of the psychoactive cannabinoid, tetrahydrocannabinol, produced therein. The present invention is further directed to a procedure for isomerizing and/or converting of cannabidiol, such as may be extracted in commercially viable amounts from industrial hemp, to tetrahydrocannabinol. Finally, one embodiment of the invention employs a first solvent to extract cannabidiol and, once the cannabidiol is isomerized, a different, second solvent is employed to extract cannabinoids.

Description of the Related Art

Various attempts have been made to extract tetrahydrocannabinol and other cannabinoid constituents present in industrial hemp in order to isolate the psychoactive cannabinoid fractions therein. At least two of the known processes require operation under supercritical conditions which, in addition to being extremely expensive to construct and operate on a commercial scale, are complicated and considerably more dangerous to operate than processes operating closer to ambient conditions. Butane and carbon dioxide are known to have been utilized as extraction "fluids" in such supercritical processes.

A further disadvantage of butane as a supercritical extraction "fluid" lies in the fact that commercial grade butane includes amounts of mercaptan to provide for odor detection, as pure butane is odorless. As such, extracts obtained via this supercritical butane extraction process also comprise unwanted amounts of mercaptan as well.

Another process utilizes ethanol as an extraction fluid, however, less than pure ethanol is often utilized, i.e., denatured ethanol, thereby allowing harmful contaminants in the denatured ethanol to pass though to the extracted cannabinoid constituents.

One crude conversion process is known to exist which begins with an oily feedstock rich in Δ8-tetrahydrocannabinolic acid ("THCA") and isomers thereof. The THCA is spread onto parchment paper or a similar substrate, and is exposed to extreme heat, such as may be provided by industrial heaters, resulting in decarboxylation and formation of the psychoactive cannabinoid fraction, tetrahydrocannabinol. As will be appreciated, such a process is inefficient and difficult to control, thus resulting in end products having widely varying amounts of conversion product, i.e., tetrahydrocannabinol.

As such, it would be beneficial to provide a safe and economical process for the extraction of cannabinoid components from industrial hemp. It would be further advantageous to have a conversion process wherein an extraction component rich in cannabidiol is converted into a conversion product rich in tetrahydrocannabinol. A further benefit may be realized by providing a process for fractionation of a conversion product into a plurality of cannabinoid classes which may subsequently be recombined in predetermined amounts in order to mimic the cannabinoid profile in well known, but difficult and/or expensive to cultivate strains of *Cannabis* plants.

SUMMARY OF THE INVENTION

The present invention is directed to a cannabidiol extraction and conversion process. In at least one embodiment, a cannabidiol extraction process includes a sizing unit wherein an amount of raw *Cannabis* plant material is reduced to a uniform size in order to maximize the extraction efficiency therefrom upon contact with one or more extraction solvents. The sizing unit may comprise a grinding or shredding apparatus as is commonly known in the field. In a preferred embodiment the raw *Cannabis* biomass is ground to about one-quarter to one-eighth of an inch in size, and can include stems, leaves, and flowers.

A blending unit is provided in at least one embodiment of a cannabidiol extraction process in accordance with the present invention wherein a first solvent is blended together with the *Cannabis* plant material to form an initial extract. A primary filtration unit and/or an extraction adsorption unit are incorporated into at least one embodiment of a conversion process in order to remove unwanted plant matter and/or other unwanted extraction byproducts from the initial extract.

In a preferred embodiment, the blending unit may comprise a centrifugal extraction system in which the sized biomass is combined with a solvent, preferably USP grade, 200 proof ethanol. The centrifugal extraction unit may be operative to agitate the biomass and ethanol mixture for a predetermined period of time to facilitate extraction. Additionally, a final centrifugal extraction cycle or a "spin" cycle may be employed to assist in draining the cannabidiol and ethanol solution from the blending unit.

Before converting the extracted cannabidiol, it may be advisable to refine the extract via one or more of a plurality of procedures. A first procedure can include winterizing the extract in order to facilitate the separation of layers from the extract, such as waxes and lipids that may have also been extracted from the initial *cannabis* biomass. The winterized extract solution may also be filtered and "dewaxed" such as by passing the solution through a variety of filters, including a diatomaceous earth filter and/or a post-activated carbon filter. In a preferred embodiment, the filters may comprise lenticular filters one the order of about 1 micron in aperture size.

Additionally, before converting the extracted cannabidiol, it may be desirable to distill and/or evaporate at least a portion of the first solvent from the extract. In a preferred embodiment, a rotary evaporator is utilized and the solution is distilled until a desired viscosity is achieved. Therefore, the isomerization process can be achieved more effectively. A visual confirmation can be utilized to determine when the solution achieves a more "oil-like" viscosity rather than a liquid solution. In an embodiment where a rotary evaporator is utilized, the visual confirmation is facilitated by watching for a change in the behavior of the fluid as it is rotated within the evaporator. Once a sufficient amount of solvent has been removed the solution can be referred to as crude cannabidiol ("CBD") oil.

As a final optional but preferred step before converting the cannabidiol extract, the crude CBD oil can be decarboxylated and devolatized according to predetermined parameters. One embodiment can include batching the crude CBD oil into two-liter batch sizes, housed in approximately four-liter beakers, and slowly heating each batch in ten-degree Celsius increments until the crude CBD oil reaches one hundred fifty degrees Celsius. The crude CBD oil is then held at one hundred fifty degrees for a period of approximately four hours or until the crude CBD oil ceases to bubble. After this point, an additional holding period of two hours at one hundred fifty degrees Celsius is recommended.

As noted above, the present invention further comprises a cannabidiol conversion process. In at least one embodiment, a cannabidiol conversion process comprises a conversion rotary reflux unit wherein the refined, processed crude CBD oil is titrated with an acidic component to form a conversion reflux which includes crude tetrahydrocannabinol ("THC") oil. In a preferred embodiment, the acidic component is NF grade sulfuric acid at ninety-nine percent. Once the conversion is complete, it is also recommended to neutralize the crude THC oil with an appropriate basic component, such as sodium hydroxide. In such a neutralization step, the titration can be considered complete once an emulsion forms. However, an emulsion is not considered advantageous for the remaining steps of the process, and instead a two-phase liquid solution is preferred. As such, a very small quantity of diluted acidic component can be added back into the mixture in order to break the emulsion and separate out the two liquid phases.

Once suitably isomerized and/or converted, and neutralized (if desired) the cannabinoids in the crude THC oil may be extracted utilizing a second solvent, which in a preferred embodiment, is dichloromethane (also known as methylene chloride). In a most preferred embodiment, a liquid-liquid extraction system may be utilized which can accomplish two steps at once. Primarily, it will introduce the cannabinoids in the crude THC oil to the dichloromethane for extraction. Secondarily, however, it will also serve to remove any remaining ethanol from the solution. As such, it will be desirable to introduce the dichloromethane via the organic phase tank of a liquid-liquid extractor. Therefore, when the extraction is complete, any remaining ethanol should be discharged into the aqueous phase discharge tank for disposal. The organic phase discharge should receive the solution of crude THC oil in dichloromethane. One benefit of such an arrangement is that the dichloromethane can be completely distilled from the solution, leaving relatively pure crude THC oil which can be further refined and/or distilled.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION

The present invention is directed to a cannabidiol extraction and conversion process, as stated above. More in particular, in at least one embodiment of the present invention, cannabidiol is extracted from a plant of the genus *Cannabis*. In yet one further embodiment, the plant of the genus *Cannabis* comprises industrial hemp which has been specifically bred to substantially limit the amount of the psychoactive cannabinoid, tetrahydrocannabinol, produced therein, in favor of the non-psychoactive cannabinoid, cannabidiol.

In at least one embodiment, the raw *Cannabis* plant material is dried to minimize the amount of water present therein which may reduce the efficiency of the extraction process. The stems, stalks, and roots of the *Cannabis* plant are cut or chopped into small pieces prior to placement into an extraction vessel. The flowers, buds, and leaves of the *Cannabis* plant, in general, do not require any size reduction prior to the extraction process. In at least one embodiment, the stems, stalks, and roots of the *Cannabis* plant are cut or chopped into pieces having a maximum dimension of about one-quarter quarter inch to about one-half inch. In one further embodiment, the raw *Cannabis* plant material is dried after being cut or chopped into small pieces, so as to facilitate the drying process.

The sized *Cannabis* plant material which, as used herein, includes the stems, stalks, and roots of the *Cannabis* plant which have been cut or chopped into pieces along with any flowers, buds, or leaves present, is placed into an extraction vessel and is substantially covered with a solvent. In one embodiment, the solvent comprises dichloromethane, i.e., $CH_2Cl_2$, and in at least one embodiment, the dichloromethane has a purity of about 95 percent.

The mixture of sized *Cannabis* plant material and dichloromethane is shaken or stirred during an initial extraction cycle until the solvent takes on color from the *Cannabis* plant material. Once the solvent has taken on color from the *Cannabis* plant material, the extraction solution is drained from the extraction vessel. The extraction cycle is repeated with fresh dichloromethane being used for each additional extraction cycle. In at least one embodiment, two additional extraction cycles are performed. The extraction solutions recovered from the extraction vessel from each of the extraction cycles are combined into a single vessel, and the remaining solid *Cannabis* plant material may be discarded.

The combined extraction solution is processed through activated carbon to adsorb solids and other unwanted components from the combined extraction solution. In at least one embodiment, granular activated carbon having an average size of about 35 to 40 microns, i.e., U.S. Mesh 400, is utilized. A contact time of the combined extraction solution with the granular activated carbon of about 20 to 45 minutes is utilized in accordance with one embodiment of the present invention.

After processing through activated carbon, in accordance with at least one embodiment of the present invention, an amount of combined extraction solution of about 20 to 50 liters is placed into a 100-liter rotary evaporator to remove excess dichloromethane. As will be appreciated by those of skill in the art, the volume of extraction solution and the volume of the evaporator can be scaled up, as needed, for large capacity production, such as is disclosed in Example 1 below with reference to the figures herein.

In at least one embodiment, the rotary evaporator operates under a slight vacuum in the range of about 400 to 600 millimeters of mercury ("mm HG"). In one further embodiment, the combined extraction solution in the rotary evaporator is maintained at a temperature in a range of about 40 to 50 degrees Celsius ("° C."), and in yet one further embodiment, the rotary evaporator is maintained at a temperature of about 43° C. The rotary evaporator, in accordance with one embodiment of the present invention, is operated at a speed in a range of about 100 to 200 revolutions per minute ("rpm").

During the rotary evaporation process, dichloromethane is removed, and a concentrated extract remains. An amount of ethanol, i.e., $C_2H_5OH$, is added to the concentrated extract in the rotary evaporator. In one embodiment, the ethanol has a purity of about 100%. The ethanol and concentrated extract are allowed to blend together in the rotary evaporator at a speed of about 100 to 200 rpm, until a homogenous solution is obtained. In at least one embodiment, the amount of ethanol added is equal to about three times the amount of the concentrated extract remaining in the rotary evaporator following the rotary evaporation process.

Following the blending process, the ethanol extract is defatted via a wax coalescing process, and in one further embodiment, a filter is utilized to collect and remove coalesced fat from the ethanol extract, leaving a processed extract comprising cannabidiol in a range of about 60% to 80% by weight.

As noted above, the present invention further comprises a process for the conversion of cannabidiol to tetrahydrocannabinol. To begin, in at least one embodiment, an amount of defatted extract comprising cannabidiol in a range of about 60% to 80% by weight is placed into a reflux reaction vessel. One drop of concentrated sulfuric acid, i.e., 95% to 98% sulfuric acid, is added to the reflux reaction vessel per gram of defatted extract. The reflux reaction is carried out under a vacuum in a range of about 400 to 600 mm HG at a temperature in arrange of about 80° C., for a time of about 2 hours.

The refluxed extract is placed into a separator with water and dichloromethane. In at least one embodiment, the amount of water added to the separator is about twice the amount of the refluxed extract, and the amount of dichloromethane added is about equal to the amount of the refluxed extract.

The separator is shaken to thoroughly mix the aqueous and organic fractions, and the resulting mixture is allowed to stand for about 30 minutes to separate into layers. In at least one embodiment, the separator is vented to atmosphere. The aqueous layer is decanted from the separator and discarded.

The remaining organic extract is then rinsed in the separator with an amount of water equal to about twice the volume of the organic extract remaining, and an amount of one normal sodium hydroxide solution, i.e., 1N NaOH, is added. In at least one embodiment, the amount of 1N NaOH solution added is equal to the amount of concentrated sulfuric acid added during the extraction process. This mixture is agitated, and the pH tested. Additional amounts of the 1N NaOH are added under agitation until the pH of the solution is about neutral, i.e., a pH of about 7.

Once the pH has been adjusted to about neutral, the solution is agitated further, vented, and is allowed to separate. The aqueous layer is once again decanted and discarded, and the remaining organic layer is rinsed with water in accordance with the foregoing procedure two additional times.

The rinsed organic extract is filtered through activated carbon to remove residual water. In at least one embodiment, the carbon filtration is performed under vacuum.

After carbon filtration, the organic extract is filtered to about 2 microns and is once again transferred into a rotary evaporator to remove dichloromethane. In at least one embodiment, an amount of ethanol is added to the oily extract in a ratio of about three parts ethanol to one part of oily extract.

A final step, in at least one embodiment, is to dry the ethanol/oil mixture in the rotary evaporator to remove any dichloromethane which remains entrapped therein, and the finished product is packaged for further use.

In accordance with at least one embodiment of the present invention, a defatted extract comprising cannabidiol in a range of about 60% to 80% by weight is converted into an ethanol/oil mixture comprising tetrahydrocannabinol in a range of about 60% to 80% by weight.

As stated above, the present invention is directed to a cannabidiol extraction and conversion process generally as shown as at 10 throughout the figures. More in particular, FIGS. 1A and 1B present one illustrative embodiment of a cannabidiol extraction process 100, while FIGS. 2A and 2B present one illustrative embodiment of a cannabidiol conversion process 200.

Figure 1A:
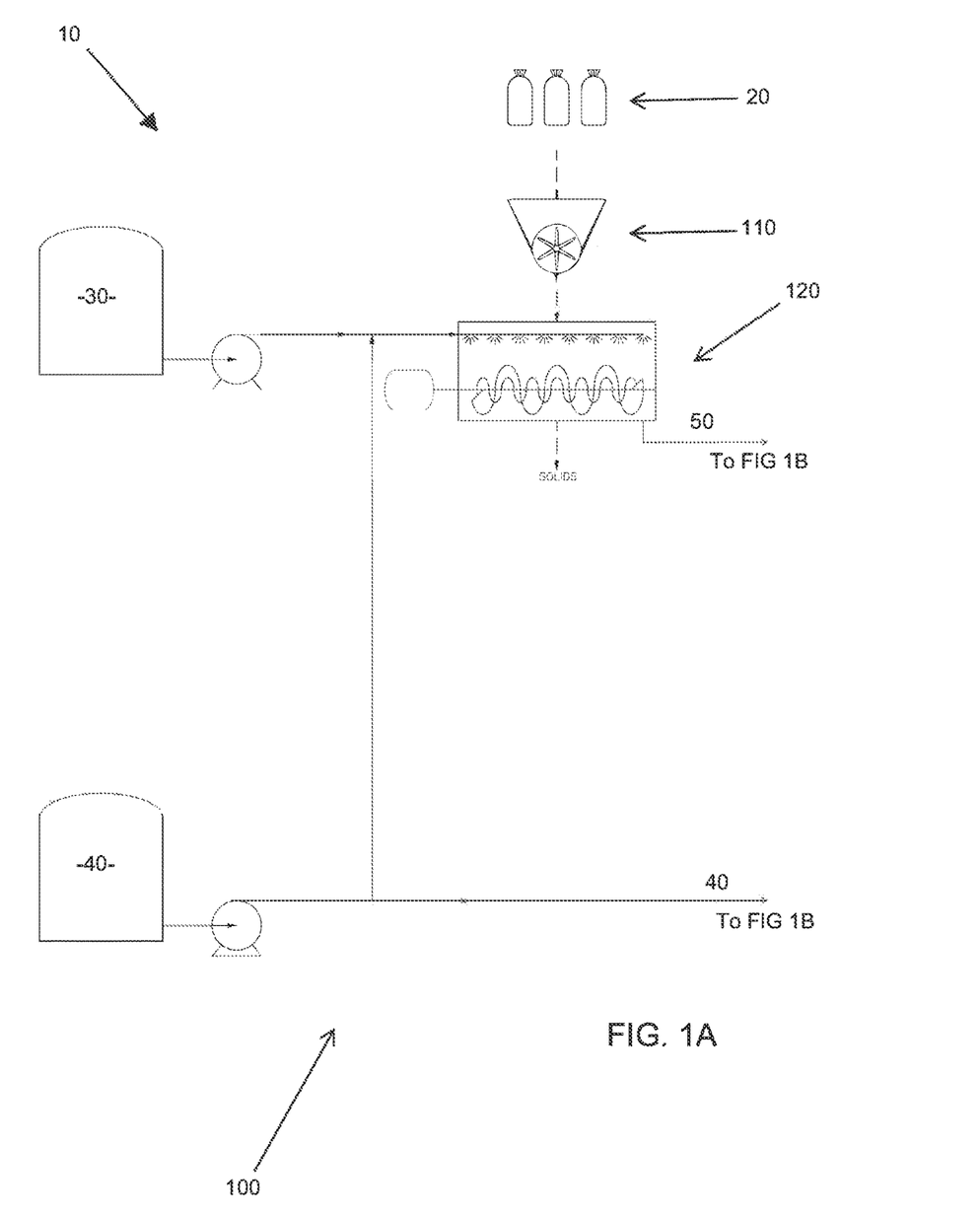
FIGS. 1A and 1B present a diagrammatic representation of one illustrative embodiment of an extraction process of a cannabidiol extraction and conversion process in accordance with the present invention.
Figure 1B:
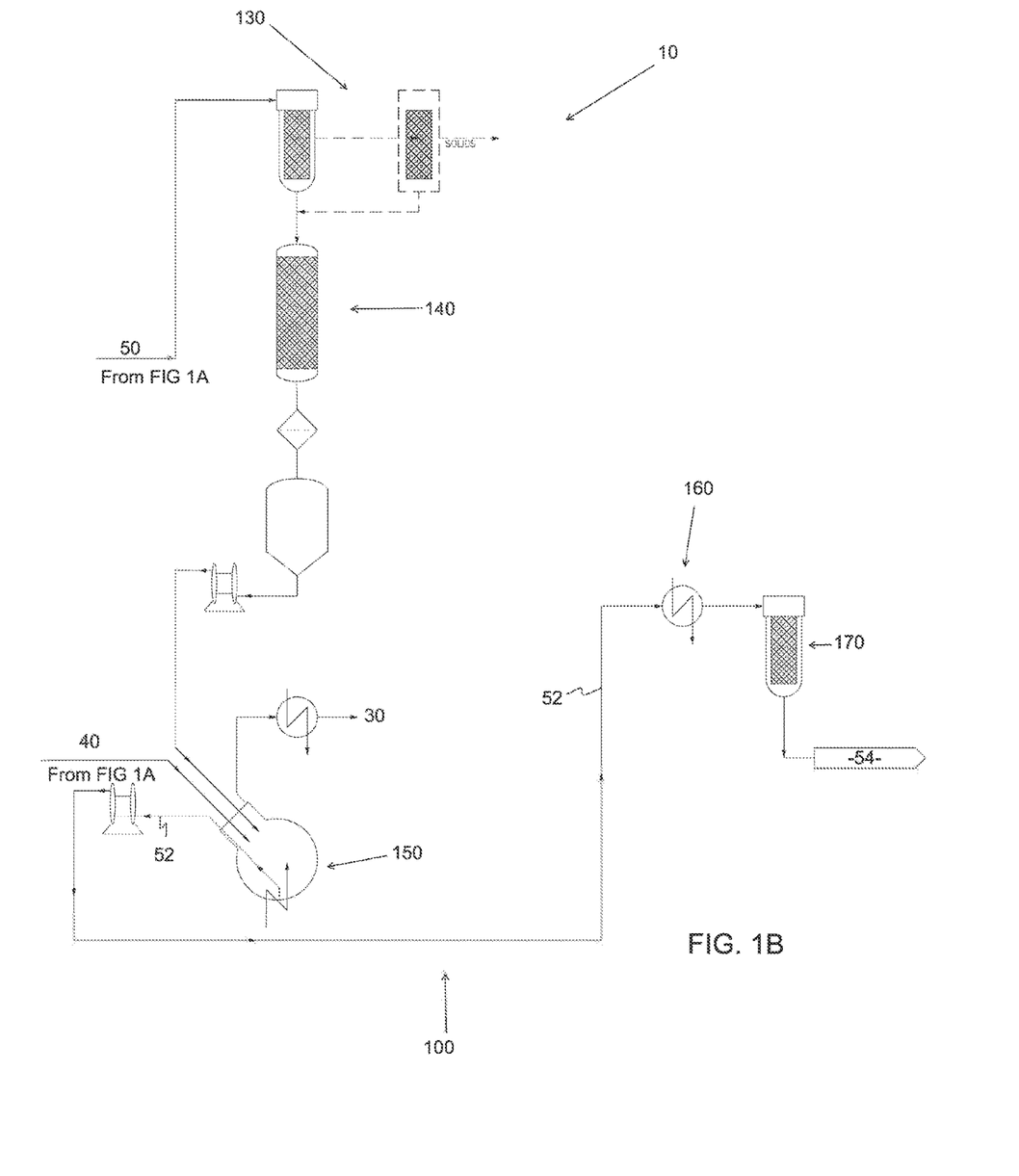
Figure 2A:
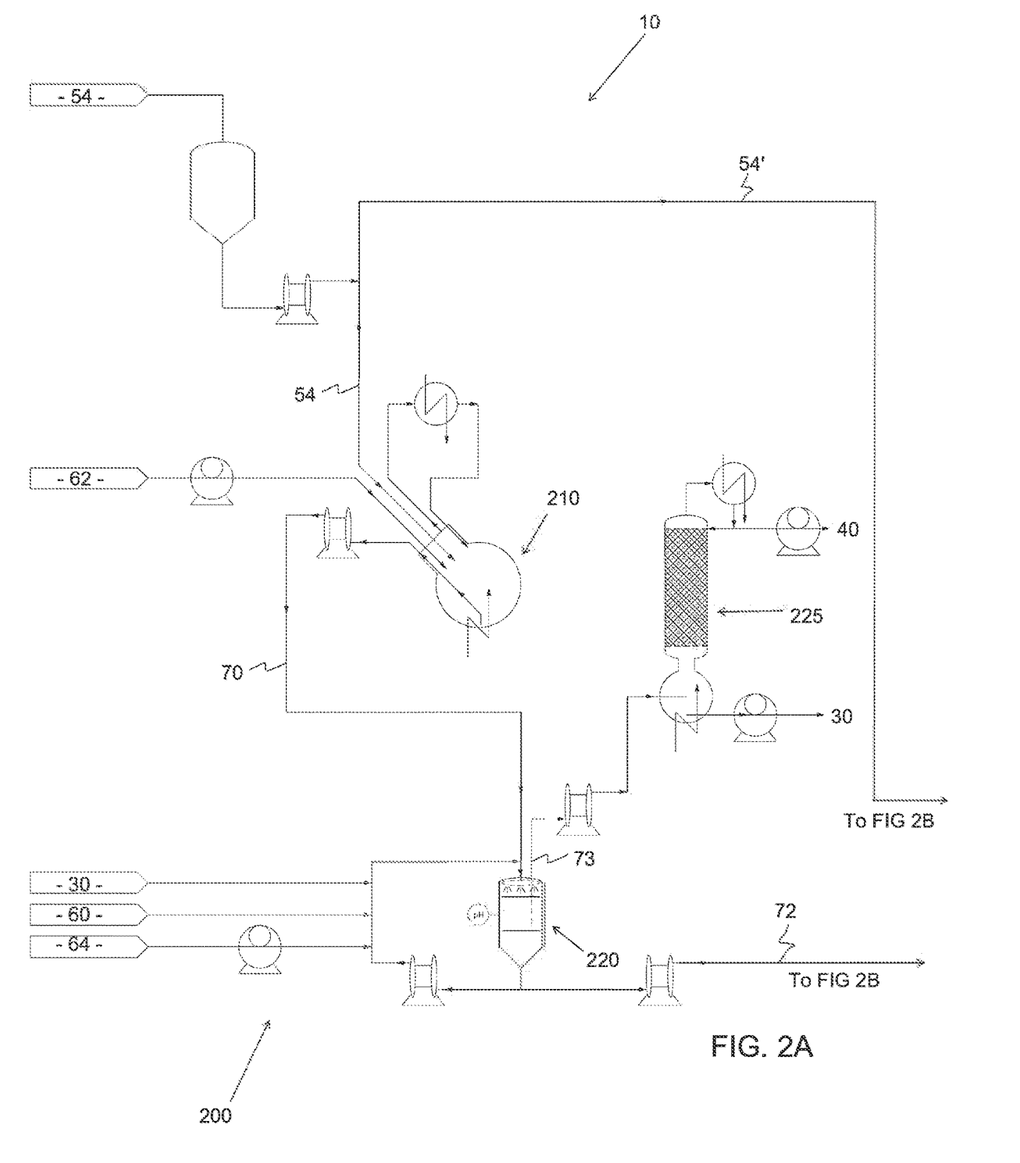
FIGS. 2A and 2B present a diagrammatic representation of one illustrative embodiment of a conversion process of a cannabidiol extraction in accordance with the present invention.
Figure 2B:
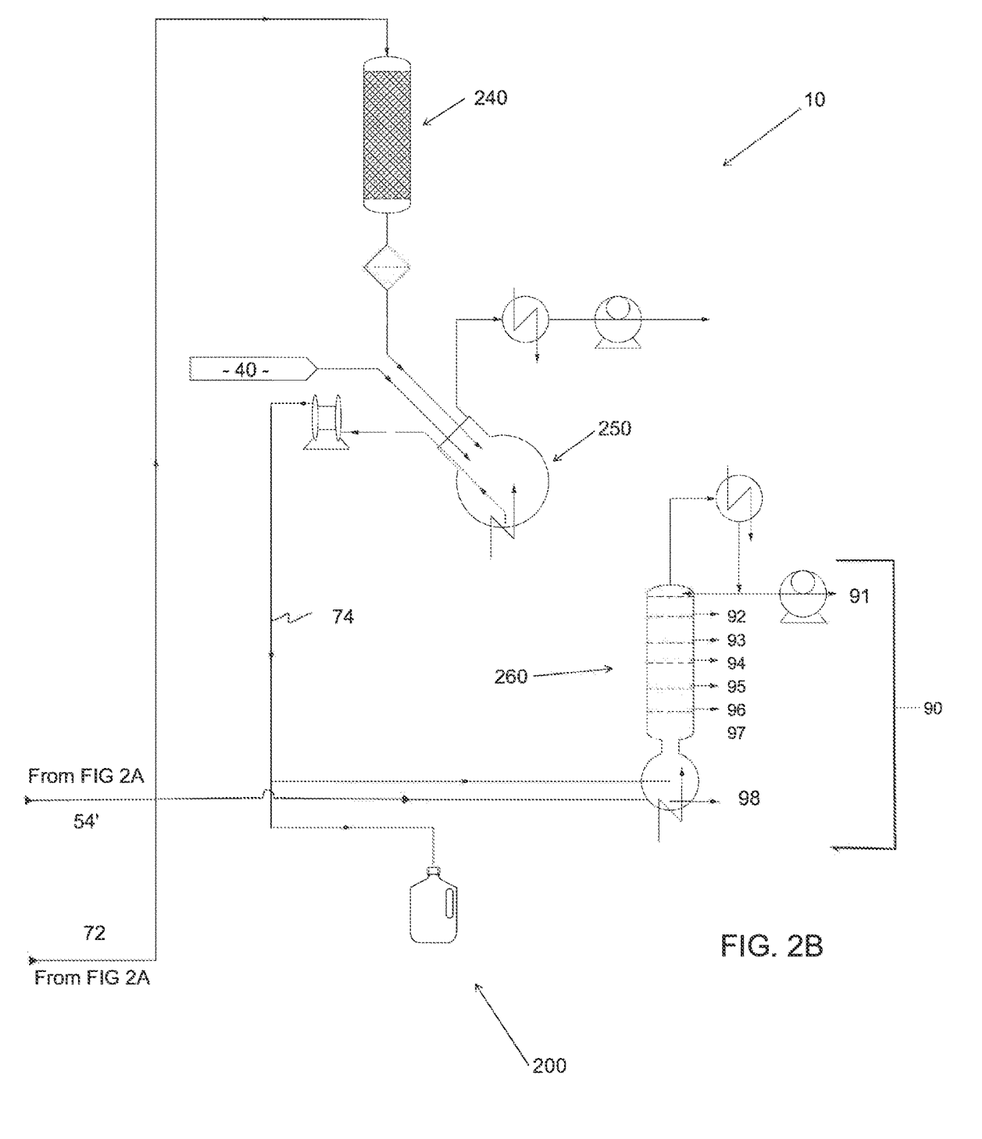

Turning first to the illustrative embodiment of a cannabidiol extraction process 100 as shown in FIGS. 1A and 1B, the process begins with an amount of raw materials, namely, raw *Cannabis* plant material 20. As before, in at least one embodiment, the raw *Cannabis* plant material 20 utilized in accordance with the present invention comprises industrial hemp varieties specifically bred to substantially limit the amount of tetrahydrocannabinol produced therein.

The extraction process further comprises at least one extraction solvent. In at least one embodiment, such as shown in FIG. 1A, an extraction process 100 in accordance with the present invention comprises a plurality of extraction solvents, namely, extraction solvent A 30 and extraction solvent B 40. In accordance with at least one embodiment of the present invention, extraction solvent A 30 comprises dichloromethane, i.e., $CH_4Cl_2$. In one further embodiment of an extraction process 100 in accordance with the present invention extraction solvent B 40 comprises ethanol, i.e., $C_2H_5OH$.

Looking further to the illustrative embodiment of FIG. 1A, the extraction process 100 comprises a sizing unit 110 which is utilized to cut, chop, etc., the raw *Cannabis* plant material 20 into an appropriate size for extraction of cannabidiol therefrom. In at least one embodiment, a sizing unit 110 reduces the raw *Cannabis* plant material 20 to pieces having a uniform maximum dimension of about one-quarter inch to one-half inch.

Following the sizing unit 110, the sized *Cannabis* plant material 20 is transferred to a blending unit 120. It is in blending unit 120 that the primary extraction occurs, and as such, amounts of extraction solvent A 30 and/or amounts of extraction solvent B 40 are introduced into blending unit 120 with a corresponding amount of sized *Cannabis* plant material 20. In at least one embodiment, the blending process utilizes solvent A 30 comprising dichloromethane, and is carried out at ambient temperature and pressure for a period of about 20 minutes, per batch, at a speed of about 30 rpm. In one further embodiment, solvent A 30 comprises dichloromethane having a purity of about 95 percent.

As further shown in the illustrative embodiment of FIG. 1A, following the primary extraction process in the blending unit 120, solid plant material is discharged, and may be discarded, and an initial extract 50 is retained for further processing.

Turning next to FIG. 1B, the initial extract 50 from blending unit 120 is directed through a primary filtration unit 130. As will be appreciated by those with skill in the art, primary filtration unit 130 may include an appropriately sized bag or screen type filter so as to remove any solid particulate plant material remaining in the initial extract 50. In at least one embodiment, primary filtration unit 130 further comprises a bag filter press for collection and removal of solid particulate matter from the initial extract 50.

With further reference to the illustrative embodiment of FIG. 1B, the present extraction process 100 further comprises an extraction adsorption unit 140. In at least one embodiment, an extraction adsorption unit 140 comprises an amount of an appropriately sized granular activated carbon material which is selected to remove specific unwanted components from initial extract 50. A contact time of about 20 to 30 minutes for the initial extract 50 in the extraction adsorption unit 140 is utilized in at least one embodiment of the present invention.

Following the extraction adsorption unit 140, the initial extract 50 is introduced into a primary solvent exchange rotary evaporator unit 150. As shown in the illustrative embodiment of FIG. 1B, an amount of solvent B 40 is also fed into the primary solvent exchange rotary evaporator unit 150. Once again, in at least one embodiment of the present extraction process 100, solvent B 40 comprises ethanol having a purity of about 100%. In one further embodiment, the amount of solvent B 40 comprising 100% ethanol added to the primary solvent exchange rotary evaporator unit 150 is about equal to the amount of initial extract 50 added thereto.

The primary solvent exchange rotary evaporator unit 150 in accordance with at least one embodiment of the present invention is operated at a temperature of about 40 to 60° C. under a vacuum of about 400 to 600 mm Hg. In accordance with at least one further embodiment, the primary solvent exchange rotary evaporator unit 150 operates at a speed in a range of about 100 to 200 rpm. In yet one further embodiment, the initial extract 50 is processed in the primary solvent exchange rotary evaporator unit 150 with solvent B 40 for a period of time in a range of about 2 to 3 hours.

An evaporated extract 52 is obtained from the primary solvent exchange rotary evaporator unit 150. Further, an amount of solvent A 30 may be recovered via a condenser unit and recycled to the solvent A 30 storage tank. The resultant evaporated extract 52 is relatively high in fatty content and as such, in at least one embodiment, the evaporated extract 52 is processed through a wax coalescing unit 160 so as to "defat" the evaporated extract 52.

In one further embodiment, a secondary extraction filtration unit 170 is employed following a wax coalescing unit 160 to collect waxes and/or fats which drop from solution in the wax coalescing unit 160, thereby resulting in an end product of one embodiment of the extraction process 100 in accordance with the present invention, namely, a processed extract 54. As will be appreciated by those of skill in the art, processed extract 54 will be relatively high in cannabidiol content. More in particular, a processed extract 54 obtained via an extraction process 100 in accordance with at least one embodiment of the present invention will comprise cannabidiol in amounts in a range of about 60% to 80% by weight.

Turning next to the illustrative embodiment presented in FIGS. 2A and 2B, a conversion process 200 in accordance with the present cannabidiol extraction and conversion process 10 is presented. As shown in the illustrative embodiment of FIG. 2A, a processed extract 54, such as may be obtained from extraction process 100 in accordance with the present invention, is a primary feedstock to a conversion process 200. More in particular, a processed extract 54 is introduced into a conversion rotary reflux unit 210 along with the amount of acidic component 62. More in particular, in at least one embodiment, acidic component 62 comprises sulfuric acid, and in one further embodiment, acidic component 62 comprises concentrated sulfuric acid, i.e., sulfuric acid at a concentration of about 95% to 98%. The acidic component 62 comprising concentrated sulfuric acid is added to a conversion rotary reflux unit 210 in an amount in a range of about 2% to 3% of the weight of the processed extract 54, in accordance with at least one embodiment of the present conversion process 200.

A conversion rotary reflux unit 210 in one embodiment is operated at a temperature of about 40 to 60° C., and under a vacuum in a range of about 400 to 600 mm Hg. In accordance with at least one embodiment, the conversion rotary reflux unit 210 operates at a speed of about 100 to 200 rpm. In yet one further embodiment, the processed extract 54 is processed in the conversion rotary reflux unit 210 for a period of about 2 to 3 hours.

Following the conversion rotary reflux unit 210, a conversion reflux 70 is introduced into a separator unit 220. As shown in the illustrative embodiment of FIG. 2A, an amount of extraction solvent A 30 is introduced into separator unit 220 with the conversion reflux 70. As before, in at least one embodiment, solvent A 30 comprises dichloromethane, and in one further embodiment, solvent A 30 comprises dichloromethane having a purity of about 95 percent. In addition, in accordance with one embodiment of the present conversion process 200, amounts of deionized water 60 and a basic component 64 are also added to separator unit 220 with the conversion reflux 70 and solvent A 30.

In accordance with one embodiment of the present conversion process 200, the amount of solvent A 30 added to the separator unit 220 is about equal to the volume of conversion reflux 70 added thereto, and the amount of deionized water 60 added to the separator unit 220 is equal to about two times the volume of conversion reflux 70. The basic component 64 comprises 1N NaOH in at least one embodiment, and is added in amounts sufficient to adjust the pH of the mixture of the conversion reflux 70, solvent A 30, and deionized water 60 in separator unit 220 to approximately neutral. Separator unit 220 operates at ambient temperature and pressure in accordance with at least one embodiment of the present conversion process 200.

As shown in the illustrative embodiment of FIG. 2A, a separator organic effluent 72 is obtained from separator unit 220. Further, a solvent layer 73, consisting primarily of solvent A 30 and/or solvent B 40 from separator unit 220, is directed to a solvent distillation unit 225 for separation and return to the respective solvent storage tanks for use in the extraction process 100.

Turning next to the illustrative embodiment of FIG. 2B, the separator organic effluent 72 is initially processed through a conversion adsorption unit 240. As with extraction adsorption unit 140, in at least one embodiment, a conversion adsorption unit 240 in accordance with the present invention comprises an amount of granular activated carbon to remove select unwanted components from the separator organic effluent 72. In at least one embodiment, a U.S. mesh 400 activated carbon in utilized in conversion adsorption unit 240. A contact time of about 20 to 45 minutes is provided for the separator organic effluent 72 in the conversion adsorption unit 240 in accordance with at least one embodiment of the present invention, and in at least one further embodiment, a contact time of about 30 to 45 minutes is provided.

Following the conversion adsorption unit 240, the separator organic effluent 72 is introduced into a secondary solvent exchange rotary evaporator unit 250. As further shown in the illustrative embodiment of FIG. 2B, an amount of solvent B 40 is also introduced into the secondary solvent exchange rotary evaporator unit 250. Solvent B 40 in at least one embodiment, as before, comprises ethanol, and in one further embodiment, solvent B 40 comprises ethanol having a concentration of about 100%. The amount of solvent B 40 added to secondary solvent exchange rotary evaporator unit 250, in one embodiment, is in a range of about one-half the volume of separator organic effluent 72 to about twice the volume of separator organic effluent 72. In at least one further embodiment, the amount of solvent B 40 added to the secondary solvent exchange rotary evaporator unit 250 is about equal to the volume of separator organic effluent 72.

In accordance with at least one embodiment of the present conversion process 200, a secondary solvent exchange rotary evaporator unit 250 is operated at a temperature of about 40 to 60° C., and under a vacuum in a range of about 400 to 600 mm Hg. In accordance with one further embodiment, a secondary solvent exchange rotary evaporator unit 250 is operated at a speed of about 100 to 200 rpm. In yet one further embodiment, the separator organic effluent 72 is processed in the secondary solvent exchange rotary evaporator unit 250 with solvent B 40 for a period of time in a range of about 1 to 4 hours, and in one further embodiment, the separator organic effluent 72 is processed in the secondary solvent exchange rotary evaporator unit 250 for about 2 hours.

After processing via the secondary solvent exchange rotary evaporator unit 250, an exchange reflux 74 is obtained from the secondary solvent exchange rotary evaporator unit 250. In accordance with at least one embodiment of the present invention, an exchange reflux 74 comprises about 60% to 80% tetrahydrocannabinol by weight.

Similar to primary solvent exchange rotary evaporator unit 150, in at least one embodiment of the present invention, a condenser is employed in combination with the secondary solvent exchange rotary evaporator unit 250 in order to recover an amount of solvent A 30 for return to solvent A 30 storage tank for further use in an extraction process 100 in accordance with the present invention.

The final step in accordance with at least one embodiment of a conversion process 200 of the present invention comprises processing an exchange reflux 74 through a fractionation unit 260. In at least one embodiment, the fractionation unit 260 separates the exchange reflux 74 into a plurality of functional fractions or classes which collectively define a conversion product 90. In accordance with at least one embodiment, the fractionation unit 260 separates the exchange reflux 74 into eight functional fractions or classes, namely, a cannabinol ("CBN") fraction 91, a tetrahydrocannabinol ("THC") fraction 92, a cannabigerol ("CBG") fraction 93, a cannabidiol ("CBD") fraction 94, a cannabichromene ("CBC") fraction 95, a cannabichromanone ("CBCN") fraction 96, a cannabifuran ("CBF") fraction 97, and a cannabielsoin ("CBE") fraction 98.

As such, the conversion product 90 in accordance with the present invention comprises functional fractions which may be selectively recombined, such as, by way of example, via blending either alone or in combination with inert carrier agents, in a manner that replicates the overall cannabinoid profile in various strains of specially grown *Cannabis* plants, and in at least one embodiment, to replicate the overall tetrahydrocannabinol profile of *Cannabis* plants exhibiting the greatest psychoactive properties.

Further, the conversion product 90 in accordance with the present invention comprises tetrahydrocannabinol which may administered via any of a number of delivery mechanisms including, at least, personal electronic vaporizing devices, more commonly known as e-cigarettes.

With reference once again to the illustrative embodiment of FIGS. 2A and 2B, and in accordance with at least one alternative embodiment of the present invention, a processed extract 54' obtained from extraction process 100 is processed directly via fractionation unit 260, bypassing the conversion rotary reflux unit 210, separator unit 220, conversion adsorption unit 240, and secondary solvent exchange unit 250. In this alternative embodiment, the fractionation unit 260 again separates the tetrahydrocannabinol and other target analytes present in the processed extract 54', albeit in lesser amounts than in exchange reflux 74, into a plurality of functional fractions which, once again, collectively define a conversion product 90. As before, the fractionation unit 260 separates the processed extract 54' into eight functional fractions, namely, a cannabinol ("CBN") fraction 91, a tetrahydrocannabinol ("THC") fraction 92, a cannabigerol ("CBG") fraction 93, a cannabidiol ("CBD") fraction 94, a cannabichromene ("CBC") fraction 95, a cannabichromanone ("CBCN") fraction 96, a cannabifuran ("CBF") fraction 97, and a cannabielsoin ("CBE") fraction 98.

Also as before, the conversion product 90 in accordance with this alternative embodiment of the present invention comprises functional fractions which may be selectively recombined in a manner that replicates the overall cannabinoid profile in various strains of specially grown *Cannabis* plants.

Of course, it will be appreciated by those of skill in the art that the foregoing extraction process 100 and conversion process 200 may be readily scaled up or down in order to increase and/or decrease throughput such as conditions may require. In at least one embodiment, the present cannabidiol extraction and conversion process 10 is sized to accommodate a feedstock input of about 115 kilograms, or approximately 250 pounds, of raw *Cannabis* plant material 20 per eight hour shift, which will produce an amount of about 35 to 45 kilograms of conversion product 90 which, once again, comprises about 60% to 80% tetrahydrocannabinol by weight.

Figure 3:
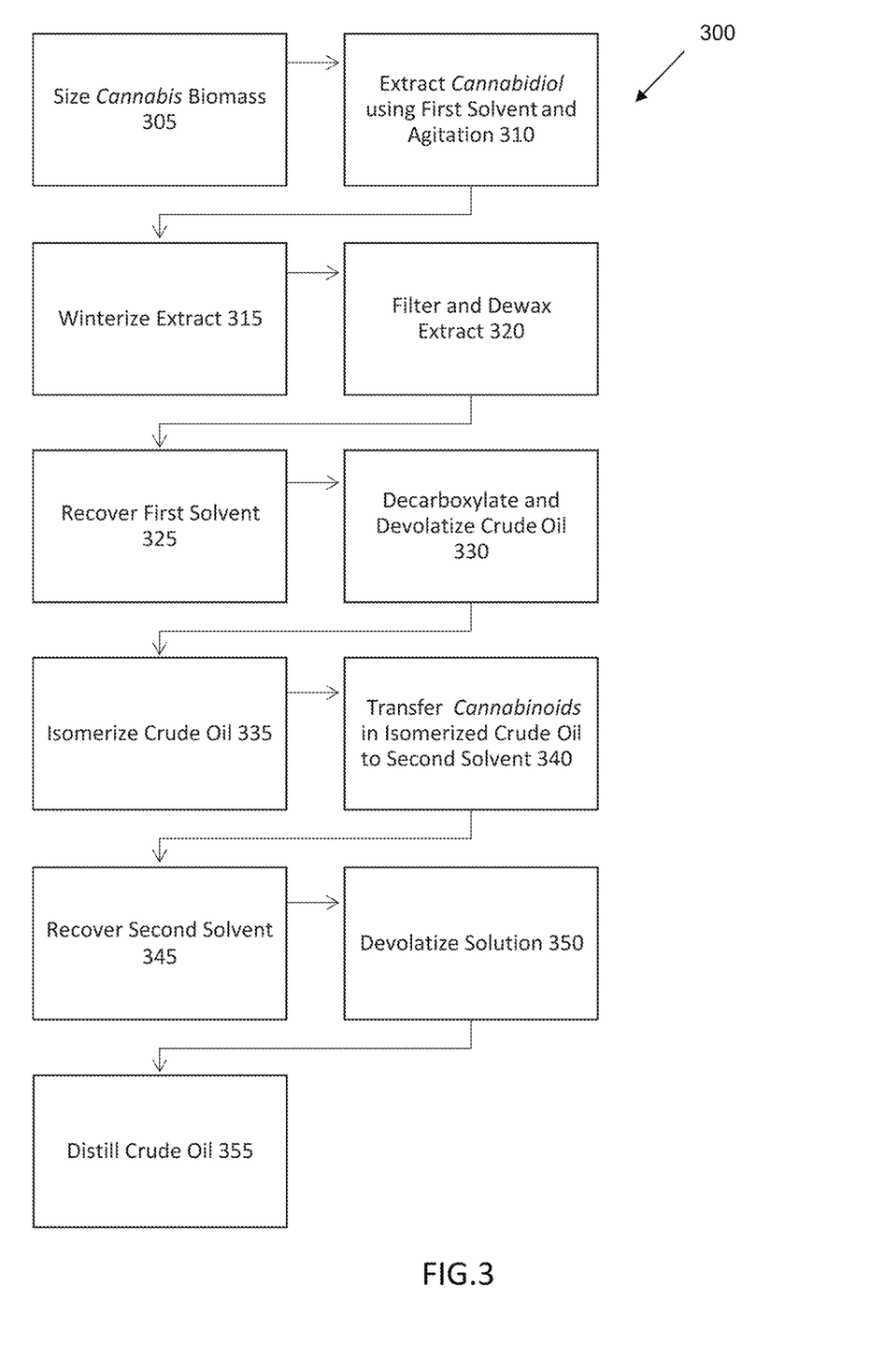
FIG. 3 is a flowchart depicting the steps of a method according to one embodiment of the present invention.

With reference to FIG. 3, the invention is also directed to another method 300 of extracting cannabidiol from *cannabis* and converting it into tetrahydrocannabinol. In a first step, 305, an amount of raw *cannabis* plant is appropriately sized for the extraction process. In a preferred embodiment, the *cannabis* biomass is ultimately placed in extraction bags having pores of approximately 100 microns. Therefore, it has been found that grinding the *cannabis* biomass to between one-eighth and one-quarter inch particle size yields desirable results.

In the next step, 310, cannabidiol is extracted from the *cannabis* biomass by exposing it to a first solvent and agitating the biomass for a predetermined period of time. In a preferred embodiment, a closed-loop, centrifugal extractor is utilized, which enhances extraction efficiency and minimizes exposure of the extract to oxygen. Once the extraction bag of biomass is placed within the extractor, pre-chilled 200 proof ethanol (as a preferred embodiment of a first solvent) is pumped into the extractor using food grade nitrogen. The volume of ethanol should be sufficient to completely submerge the biomass. Once the extractor is prepared, agitation can begin which, in a preferred embodiment, may last for between fifteen to thirty minutes. The result of step 310 is a solution of cannabidiol ("CBD") oil and ethanol according to the preferred embodiment. Steps 305-310 may be repeated until a desired batch size is achieved, such as if a discharge keg for holding the resulting solution is larger than the capacity of the extractor. Multiple extraction cycles can be run to fill a given size discharge keg, e.g., thirty gallons.

In step 315, the resulting solution of CBD oil and ethanol is winterized in order to partially refine the solution and precipitate out waxes, lipids, and other undesired compounds. In a preferred embodiment, the discharge keg from step 310 is winterized for between forty-eight to seventy-two hours at a temperature of minus twenty-five degrees Celsius or below.

In step 320, the winterized solution is filtered and dewaxed in a multi-stage process. First, while still at or near winterization temperatures, the winterized solution is pushed through a first lenticular filter having a 1-micron diatomaceous earth medium. In a preferred embodiment, the winterized solution is pushed through the filter using food grade nitrogen to avoid oxidation. Once filtered a first time, the filtered, winterized solution is allowed to warm to room temperature before being pushed through a second lenticular filter having a 1-micron post-activated carbon medium.

After filtrations and dewaxing, the first solvent may be at least partially recovered in step 325. In a preferred embodiment recovery is performed in a rotary evaporator and conducted via distillation. Parameters for recovery, such as temperature and pressure, may vary depending upon the particular solvent utilized as the first solvent. In a preferred embodiment, visual analysis is employed to determine when a sufficient amount of the first solvent has been recovered. More specifically, before recovery, the solution will tend to behave as though it is aqueous, flowing relatively freely with low viscosity. The desired viscosity, however, is closer to oil, and once a sufficient quantity of solvent is recovered, the solution may tend to form visible layers as it is rotated in the flask of the rotary evaporator.

Once a sufficient amount of ethanol has been removed, the remaining solution is largely comprised of crude CBD oil, and will be referred to as such to aid in discussion, although it may contain remnants of the first solvent and/or other compounds. However, the next step is to decarboxylate and devolatize the crude CBD oil 330. To do so, the crude CBD oil is heated, agitated, and held for a predetermined period of time until any carboxyl groups are released within the crude CBD oil. In a preferred embodiment, the crude CBD oil is slowly heated in ten degree increments to one hundred fifty degrees Celsius until it ceases to bubble or at least four hours. The crude CBD is held at one hundred fifty degrees Celsius for an additional two hours after it ceases to bubble. Additionally, a hot plate containing magnetic stir bars may be utilized to agitate the crude CBD oil during the process. Six hundred revolutions per minute has been found to be an effective speed. Moreover, in a most preferred embodiment, the crude CBD oil is decarboxylated and devolatized in four-liter beakers, having been decanted into batches of no more than two liters per beaker.

The crude CBD oil is now ready to be isomerized as in step 335. The decarboxylated and devolatized crude CBD oil is dissolved at a ratio of one part crude CBD oil to five parts solvent. In a preferred embodiment the solvent is two hundred proof ethanol. The dissolved solution is then placed in conversion reflux unit, such as a rotary evaporator with reflux apparatus. Before beginning the reflux process, a strong acid is titrated into the dissolved solution. In a preferred embodiment, the acid is 99% sulfuric acid at a ratio of two- and one-half milliliters of titrant (sulfuric acid) for every ten liters of titrand (solution of crude CBD oil and ethanol). Once the isomerization has occurred, the solution should include at least some tetrahydrocannabinol compounds suspended in oil. Therefore, to aid in discussion, the isomerized solution will be referred to as crude THC oil even though it may contain other compounds.

In a preferred embodiment, sodium hydroxide is then titrated into the solution at a rate of between three to five milliliters of sodium hydroxide for every ten liters of solution in order to neutralize the pH level. Once neutralized, an emulsion is formed, which can be broken by adding small quantities of a diluted acid solution to separate the two liquid phases, i.e., crude THC oil and ethanol.

The next step 340 involves the transfer of cannabinoids in the crude THC oil to a second solvent, which in a preferred embodiment is dichloromethane. In a preferred embodiment, a liquid-liquid extractor having organic and aqueous phase tanks is employed to do so. The second solvent is placed in the organic phase tank and the solution of crude THC oil and ethanol is placed in the aqueous phase tank. Once complete, the aqueous phase discharge can be disposed according to protocol, while the organic phase should include a solution of crude THC oil and the second solvent.

The next step of recovering the second solvent 345 may include placing the solution of crude THC oil and the second solvent into a rotary evaporator and distilling the solution until all dichloromethane has evaporated from the solution, leaving crude THC oil.

Finally, the crude THC oil is ready for distillation, as in step 355, but first it may be desirable to add a small amount of 200 proof USP Ethanol (e.g., two to three percent by weight) to the crude THC oil for ease of transfer into distillation vessels. If so, the solution must be again devolatized, as in step 350, which in a preferred embodiment is conducted at one hundred degrees Celsius for one to two hours.

In a preferred embodiment, the distillation of the crude THC oil 355 is performed in a wiped film evaporator in at least two passes. During the first pass, terpenes and runoffs are collected in separate flasks. The first pass runoff is then reintroduced into the wiped film evaporator for a second pass.

Since many modifications, variations and changes in detail can be made to the described embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A cannabidiol extraction and isomerization method comprising:
   sizing an amount of *Cannabis* plant material and extracting a solution of Cannabidiol (CBD) from the *Cannabis* plant material using a first solvent;
   winterizing the extracted solution of CBD and first solvent;
   dewaxing and filtering the extracted solution of CBD and first solvent;
   at least partially recovering the first solvent leaving a solution including crude CBD oil;

decarboxylating and devolatizing the solution including crude CBD oil;

isomerizing the solution including crude CBD oil, using an acidic catalyst, into an isomerized solution including, at least partially, crude tetrahydrocannabinol (THC) oil;

transferring cannabinoids from the isomerized solution to a second solvent;

at least partially recovering the second solvent leaving crude THC oil; and distilling the crude THC oil.

2. The method as recited in claim 1 wherein said first solvent in ethanol.

3. The method as recited in claim 1 wherein said second solvent is dichloromethane.

4. The method as recited in claim 1 wherein said *Cannabis* plant material is industrial hemp which has been bred to substantially limit the amount of psychoactive substances therein.

5. The method as recited in claim 1 wherein the step of winterizing the solution of ethanol and CBD comprises holding the solution at a maximum temperature of negative twenty-five degrees Celsius for a minimum of forty-eight hours.

6. The method as recited in claim 1 wherein the step of dewaxing and filtering further comprises running the solution through a first lenticular filter having a filter medium including diatomaceous earth.

7. The method a recited in claim 6 wherein the step of dewaxing and filtering further comprises running the solution through a second lenticular filter having a filter medium including post-activated carbon.

8. The method as recited in claim 1 wherein the step of at least partially recovering the first solvent is accomplished in a rotary evaporator.

9. The method as recited in claim 1 wherein the step of decarboxylating and devolatizing the solution includes heating the solution in ten-degree Celsius increments until the solution reaches one hundred and fifty degrees Celsius.

10. The method as recited in claim 9 wherein the step of decarboxylating and devolatizing the solution includes holding the solution at one hundred fifty degrees for at least four hours.

11. The method as recited in claim 9 wherein the step of decarboxylating and devolatizing the solution includes holding the solution at one hundred fifty degrees until the solution ceases to bubble.

12. The method as recited in claim 1 wherein the step of isomerizing the solution includes titrating sulfuric acid into the solution.

13. The method as recited in claim 12 wherein the step of isomerizing the solution includes neutralizing the solution by titrating a quantity of sodium hydroxide until an emulsion forms.

14. The method as recited in claim 13 wherein the step of isomerizing the solution includes breaking the emulsion by adding a small quantity of diluted acid solution.

15. The method as recited in claim 1 wherein the second solvent is dichloromethane.

16. The method as recited in claim 1 wherein the step of transferring the cannabinoids to a second solution is accomplished via a liquid-liquid extraction system.

17. The method as recited in claim 1 wherein the second solvent is fully recovered.

18. The method as recited in claim 1 wherein the step of distilling the crude THC oil is accomplished via a wiped film evaporator.

\* \* \* \* \*